United States Patent [19]
Riccitelli et al.

[11] Patent Number: 5,124,129
[45] Date of Patent: Jun. 23, 1992

[54] CARBON DIOXIDE INDICATOR

[75] Inventors: Samuel D. Riccitelli, Murrieta, Calif.;
John F. Goodman, Huntington, N.Y.;
Neil Dunski, St. Louis, Mo.

[73] Assignee: Mallinckrodt Medical, Inc., St. Louis, Mo.

[21] Appl. No.: 471,065

[22] Filed: Jan. 29, 1990

Related U.S. Application Data

[63] Continuation-in-part of Ser. No. 225,754, Aug. 24, 1988, abandoned, and a continuation-in-part of Ser. No. 318,002, Mar. 2, 1989, abandoned, which is a continuation-in-part of Ser. No. 325,754, Aug. 24, 1988, abandoned.

[51] Int. Cl.⁵ .................................... G01N 21/64
[52] U.S. Cl. .................................... 422/56; 422/57;
422/58; 436/68; 436/133; 436/163; 436/169;
128/719; 128/207.14
[58] Field of Search .................... 422/56–60;
436/68, 133, 163, 169, 170; 128/719, 207.14

[56] References Cited

U.S. PATENT DOCUMENTS

| | | | |
|---|---|---|---|
| 2,890,177 | 6/1959 | Kilmer | 252/408 |
| 3,068,073 | 12/1962 | Stanford | 23/232 |
| 3,114,610 | 12/1963 | Gafford et al. | 23/255 |
| 3,114,640 | 12/1963 | Vanzo | 99/103 |
| 3,420,635 | 1/1969 | Davis | 23/253 |
| 4,019,862 | 4/1977 | Dahms | 436/133 |
| 4,277,251 | 7/1981 | Leichnitz | 23/232 |
| 4,287,153 | 9/1981 | Towsend | 422/56 |
| 4,332,771 | 6/1982 | Leichnitz | 422/84 |
| 4,438,067 | 3/1984 | Siddiqi | 422/56 |
| 4,557,900 | 10/1985 | Heitzmann | 422/55 |
| 4,691,701 | 9/1987 | Williams | 128/207 |
| 4,728,499 | 3/1988 | Fehder | 422/56 |
| 4,780,411 | 10/1988 | Piejko et al. | 422/56 |
| 4,788,153 | 11/1988 | Detwiler et al. | 436/97 |
| 4,790,327 | 12/1988 | Despotis | 128/719 |
| 4,824,640 | 4/1989 | Hildebrand et al. | 422/56 |
| 4,999,306 | 3/1991 | Yafuso et al. | 436/163 |

FOREIGN PATENT DOCUMENTS 0257916 8/1986 European Pat. Off.

OTHER PUBLICATIONS

European Search Report.

*Primary Examiner*—Jill A. Johnston
*Assistant Examiner*—Lyle A. Alexander
*Attorney, Agent, or Firm*—Rothwell, Figg, Ernst & Kurz

[57] ABSTRACT

A carbon dioxide indicator for use in determining the proper placement of endotracheal tubes. The indicator is comprised of a pH-sensitive dye suspended in a predominantly hydrophilic polymer matrix. The indicator may be placed inside a tube or connector to form an indicator device. When the pH-sensitive dye changes color due to $CO_2$ and moisture in exhaled air, the color change is visible from outside the device.

59 Claims, 3 Drawing Sheets

5,124,129

CARBON DIOXIDE INDICATOR

CROSS REFERENCE TO RELATED APPLICATIONS

The present application is a continuation-in-part of co-pending U.S. patent application Ser. Nos. 07/225,754, filed Aug. 24, 1988 now abandoned, and 07/318,002, filed Mar. 2, 1989 now abandoned, which is a continuation-in-part of U.S. patent applications Ser. No. 07/225,754, filed Aug. 24, 1988 now abandoned.

BACKGROUND OF THE INVENTION

1. Field of the Invention

This invention relates to an indicator device, more particularly a rapid response device for the detection of carbon dioxide in a gas mixture.

2. Description of the Background Art

Devices for the detection of carbon dioxide which rely in part upon the change in color of certain chemical compounds according to the pH of their environment are known in the art. Such chemical indicators change color in solution when the pH of the solution changes.

Numerous examples of chemical indicators which are pH-sensitive, and thereby useful in carbon dioxide indicator systems, have been disclosed in the prior art.

U.S. Pat. No. 2,890,177 discloses a liquid chemical indicator for detecting the presence of carbon dioxide in respiratory gases comprising an aqueous solution of an alkali metal oxalate and a pH sensitive dye which changes color at a pH in the range of 6.6 to 5.8.

U.S Pat. No. 3,068,073 discloses a method for determining carbon dioxide in a gas which comprises passing the gas to be tested through a solid reagent comprising activated alumina carrying thymol blue and, optionally, a base.

U.S. Pat. No. 3,114,610 discloses a continous sampling gas analyzer comprising a pH sensitive dye suspended in a gel substance, a semi-permeable membrane which separates the gas to be tested from the dye but allows gas to pass therebetween for analysis, a light source for illuminating the dye and a detector for analyzing the light transmitted through said dye. For carbon dioxide determination the dyes disclosed are Methyl Red and Bromocresol Green.

However, none of the above patents directly addresses the problem of determining accurately and rapidly the correct positioning of an endotracheal catheter in the trachea of an apneic patient.

Introduction of a catheter in the trachea of a human may be required for a number of reasons. For example, in a hospital, an endotracheal catheter, also known as an intratracheal catheter, may be used for general anesthesia; in the field, a doctor or paramedic may use an endotracheal catheter to resuscitate an apneic patient. In both of these instances, and others, it is critical that the catheter be properly placed in the trachea and not, for example, in the esophagus. If the catheter is improperly placed and the error is not discovered within a very short time, on the order of 5 to 20 seconds, the patient may begin to suffer irreparable harm or even death.

In view of the criticality of the timing when an endotracheal catheter is improperly placed in an apneic patient, there is clearly a need for a simple device which will rapidly and reliably give an indication of improper (or proper) placement. (See P. K. Birmingham et al., "Esophageal Intubation", ANESTH ANALG, 1986, 65, 886–91).

One device for determining the correct location of an endotracheal tube is describe in U.S. Pat. No. 4,691,701 to Williams. In Williams the detector includes a housing and an indicator in the form of a transparent disc which covers an aperture in the housing. The disc has a chemical substance which provides a color change indication when exposed to carbon dioxide from the patient.

Another device for determining the correct placement of an endotracheal tube is described in U.S. Pat. No. 4,728,499 to Fehder. The device in Fehder comprises an enclosure defined by walls and having a transparent window in a wall, an inlet, an outlet and sealing means, the enclosure having mounted therein an indicator component adapted to be viewed through said transparent window. The component comprises a carrier having attached thereto an indicating element formed for (1) an aqueous solution of a colorless compound, i.e., a base, which provides an alkaline solution; (2) a hygroscopic, high boiling, transparent, colorless, water-miscible liquid; and (3) a chemogenic pH-sensitive indicator which changes color relative to a change in pH of the solution and which has a pH which is lower by 1.0–1.5 pH units than the pH of the solution. The nature and concentration of the colorless compound in (1) is correlated to the nature and concentration of indicator (3) so that no color change occurs for at least 15 minutes when the indicating element is exposed to an atmosphere having a concentration of 0.03% carbon dioxide, but a color change is produced within 5 to 10 seconds, when the indicating element is exposed to an atmosphere containing at least 2% carbon dioxide.

A carrier particularly preferred by Fehder is a thin layer of bibulous material, such as filter paper or fibrous synthetic material, and the indicating component is formed by impregnating the bibulous material with the indicating element and drying to remove excess moisture.

However, a deficiency common to the above two devices is that they are composed of small parts which must be assembled prior to use. Further, because of their structures, they are designed to be used at the end of an endotracheal tube and not inside an endotracheal tube. There therefore exists a need for a carbon dioxide indicator which is structurally simple, easy to assemble and capable of being used anywhere in a respiratory circuit, such as inside an endotracheal or other tube in the circuit, or inside a connector which joins tubes in the circuit.

SUMMARY OF THE INVENTION

In accordance with the present invention, a carbon dioxide indicator comprises a pH-sensitive dye present in a polymeric. The indicator does not rapidly change color when exposed to ambient air, but does rapidly change color when exposed directly to air exhaled from a human. Such color change upon exposure to exhale air is at least fifty times faster than when exposed merely to normal ambient air.

The invention also provides a carbon dioxide indicator device employing the indicator and methods of making such a device. The device is designed so that the color change of the indicator is viewable from outside the device. The device may be a separate piece which is a part of an endotracheal tube circuit or applied to a portion of the inner surface of an endotracheal tube.

DETAILED DESCRIPTION OF THE PREFERRED EMBODIMENTS

Figure 1:
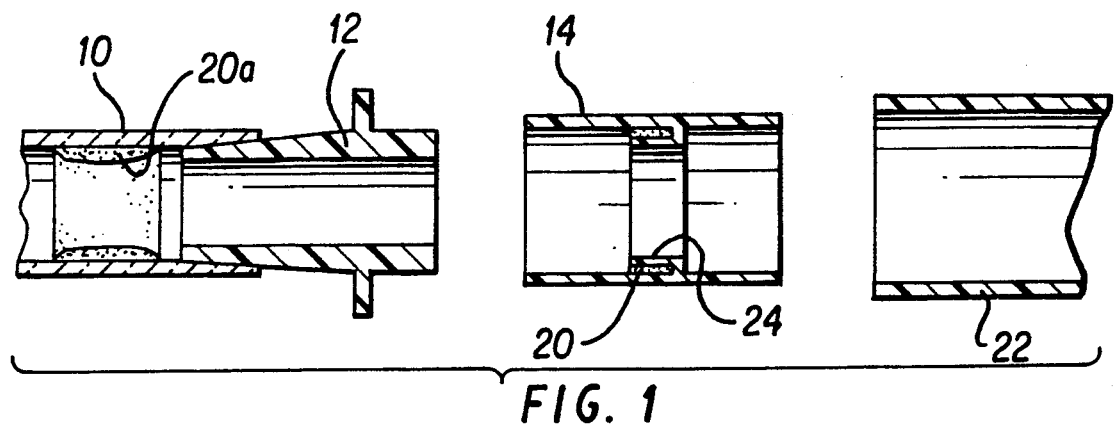
FIG. 1 shows a partially exploded, cross-sectional view of one embodiment of the invention showing two possible locations of $CO_2$ indicator material.

In the invention, a pH-sensitive dye is suspended in a polymer matrix. Suitable dyes for the purposes of the invention advantageously undergo a color change as a result of a decrease in the pH in the matrix of 1 to 5 pH units due to an influx of $CO_2$ from a patient's breath. The pH change results from the generation of carbonic acid by the reaction of $CO_2$ with moisture in the patient's breath, which generally is about 15–50 mg of water per liter of air, depending on temperature. The reaction which produces the carbonic acid occurs in the water trapped in the matrix in which the pH-sensitive dye is suspended. A preferred pH-sensitive dye is o-cresolphthalein complexon sodium salt (a calcium indicator derived from the pH indicator o-cresol-phthalein and having an active region between about pH 9.8 and 8.2).

Ambient concentration levels of carbon dioxide in the esophagus are generally about equal to normal ambient air, i.e., less than about 1 mm Hg. In contrast, concentrations of carbon dioxide in expired breath typically range between about 30 and 40 mm Hg.

In accordance with the invention, the indicator dye does not rapidly change color when exposed to the $CO_2$ levels present in normal ambient air, or upon exposure to the low $CO_2$ levels that might occur in the esophagus. In particularly preferred embodiments, the dye does not substantially respond to $CO_2$ present in ambient air for hours, days, weeks, months, or even years of continuous exposure.

According to the invention, the indicator dye changes color at least about 50 times faster when directly exposed to exhaled air than when exposed to normal ambient air.

In a preferred embodiment, the dye rapidly changes color when exposed to only one or two breaths of exhaled air, containing, for example, as little as 15 mm of Hg of carbon dioxide (approximately 2% $CO_2$). For example, the present invention can provide a rapid color change with only one exhaled breath of a patient.

At 1 mm Hg of carbon dioxide, o-cresolphthalein complexon sodium salt is purple/red (dry) or red (wet). However, at a concentration of $CO_2$ of about 15 mm of Hg, the dye turns clear. Therefore, when o-cresolphthalein complexon sodium is used as the indicator, a rapid change of color from red or purple-red in the indicator's resting state, to clear in the indicator's indicating state, indicates proper placement of an endotracheal tube in the patient's trachea.

The polymer matrix of the present invention is predominantly hydrophilic, with an optional hydrophobic portion. In preferred embodiments, the polymeric matrix includes a hydrophobic alkyl methacrylate in which the alkyl contains from one to about twelve carbon atoms. In more preferred embodiments, the matrix contains a mixture of alkyl methacrylates having alkyl portions containing from about one to twelve carbon atoms. The alkyl methacrylate(s) present in the matrix can have alkyl portions containing from one to about eight carbon atoms and/or from one to about four atoms, such as methyl methacrylate, ethyl methacrylate and the like. In particularly preferred embodiments, the hydrophobic alkyl methacrylate combination in the matrix includes an alkyl methacrylate having a relatively large alkyl side group, such as lauryl methacrylate, along with one or more alkyl methacrylate(s) having a relatively small alkyl side group, such methyl methacrylate, ethyl methacrylate, and the like.

In the preferred embodiment, the matrix is predominantly hydrophilic. In one embodiment, the ratio of hydrophilic to hydrophobic portions of the matrix is about 2:1 by weight.

As in the prior application, suitable polymers for use in the polymer matrix include hydrogels, polyurethane foams and combinations of hydrogels and hygroscopic polyurethane forms. The polymer matrix used in a particular application is advantageously chosen to afford the easiest application, the greatest hygroscopy, the fastest rate of $CO_2$ diffusion, the proper pH effect, and the best dye compatibility with the particular dye used. Suitable components for use in the polymer matrix may be selected from a list including, but not limited to, the methyl chloride quaternary salt of dimethyl methacrylate, the methyl chloride quaternary salt of dimethylaminoethyl methacrylate, hydroxethyl methacrylate, lauryl methacrylate (alone or as a copolymer with any of the above methacrylates) polyvinylpyrrolidone (alone or as a copolymer with any of the above), polyethylene oxide and/or polypropylene oxide derivatives (alone or as copolymers with any of the above), hydrogels from corn starch derivatives (referred to as "super slurpers", alone or as copolymers with any of the above), and any of the above polymers which have been cross-linked (e.g., with ethylene glycol dimethacrylate).

One possible polyurethane polymer for use with a hydrogel is Hypol, available from WR Grace. When combined with water, Hypol forms an open-celled foam to which a corn starch based hydrogel, "super slurper," (e.g. Water Lock ®, from the Grain Processing Corporation) may be added. Incorporation of a super slurper imparts to the foam a greater efficiency in capturing water from the expired breath, therefore making the device more efficient.

In one embodiment, the matrix includes a methyl chloride quaternary salt of at least one methacrylate. In a preferred embodiment, the hydrophilic portion of the matrix is an alkyl halide quaternary salt of an alkyl methacrylate, such as the methyl chloride quaternary salt of dimethylaminoethyl methacrylate. The matrix of the present invention has been found to be quite efficient in capturing water from expired breath, and also facilitates the achievement of a proper pH environment around the dye.

In accordance with one embodiment, when a hydrophobic monomer is used in the matrix, less than about 30% of the monomers utilizes are hydrophobic, the remainind monomers being hydrophilic so that the matrix as a whole is predominantly hydrophilic. In preferred embodiments, about 5% or less of the monomers employed are hydrophobic, although it is envisioned that 10%, 20% or even 30% may be suitable in some formulations.

The matrix of the present invention also improves the reversal time of the indicator dye, i.e., the amount of time that the indicator takes to change back to its original color from its indicating color (or lack of color) when the indicator is no longer exposed to $CO_2$.

The reversal time of the indicator dye is dependent on, among other things, the ratio of polymer to dye. In general, the greater the polymer to dye ratio, the slower the reversal time. With higher polymer/dye ratios, the reversal time can be as much as 5–15 minutes, while with smaller ratios the reversal time can be as short as 5–10 seconds.

If desired, a solid desiccant such as $CaCl_2$ or $MgSo_4$ may be incorporated into the matrix. A desiccant may serve to reduce the breath response time by improving the efficiency of the matrix at removing water from expired breath. When using calcium dyes such as o-cresolphthalein complexon sodium salt, the use of a calcium salt as a desiccant may increase the vividness of the color in the resting, non-indicating state of the indicator. Basic salts, such as sodium hydroxide, potassium hydroxide potassium phosphate, trisodium phosphate, and the like, have been found to enhance color when present in the matrix.

The polymer matrix containing the pH sensitive dye may be applied at any suitable location in the respiratory circuit, such as to the interior surface of a tube or other device in the circuit, including heat/moisture exchangers and the like. Surface application of the matrix can be by conventional means, such as spin coating, dip coating, spraying, coextruding, insert molding, gluing, solvent bonding, or ultrasonic welding.

A preferred method of making the device of the invention is to apply the indicator to a 15 mm endotracheal tube connector by attaching the connector to the coating shaft of an electric motor, i.e., "spin" coating. This method allows the indicator to be applied at a surface concentration of 0.05 ml per $cm^2$ of surface area. After applying the indicator to the connector, heat applied by conventional means to drive off water and set up the indicator for use. The indicator is preferably set up dry because this makes the indicator easier to handle and sterilize.

One embodiment involves converting the indicator into a UV curable system through the addition of a photo-initiator such as Ciba-Geigy's photo-initiators numbers 651 and 184. In this embodiment the polymer matrix is preferably methacrylate based and most preferably consists of greater than 70% of the methylchloride quaternary salt of dimethylaminoethyl methacrylate with less than 30% lauryl methacrylate. This polymer matrix lends itself particularly well to UV-photopolymerization.

One method of making the device of this embodiment is by in situ cross/linking. In this method the non-cross-linked co-polymer based upon the two monomers mentioned above is made using a free radical initiator and heat. A suitable free radical initiator is benzoyl peroxide. The polymer solution is then diluted with methanol. A pH-sensitive dye, base salts, and desiccants are then added. A cross-linking agent and a photo-initiator are then added in small quantities i.e., less than 10%, to the above solution matrix. A suitable cross-linking agent is ethylene glycol dimethacrylate and a suitable photo-initiator is Ciba-Geigy number 651. The solution matrix is then spin coated onto a 15 mm connector and heated to evaporate the solvent. Finally, the connector and matrix are exposed to UV radiation from a conventional UV source e.g. a Dymax PC-3. Alternatively, UV exposure may occur prior to solvent evaporation. The UV radiation induces the formation of cross-links in the matrix and thereby renders it insoluble.

In one in situ polymerization method a solution is made up containing in the proper ratio the following: both unpolymerized monomers, a photo-initiator, a cross-linker, a dye, base salts, and desiccants. Preferably methanol is also added as a diluent. The solution is then spin-coated onto a 15 mm connector and then exposed to UV radiation. In forming the coating in this way, the polymerization and cross-linking both take place simultaneously on the connector surface. The process lends itself to a highly manufacturable indicator. The coating is insoluble and therefore easily sterilizable by ethylene oxide.

Advantages in using either method to make an indicator device are that the processing time for the application of the $CO_2$ indicator matrix is reduced, the water solubility potential of the matrix is eliminated, thereby making ethylene oxide sterilization possible, and the dye more thoroughly trapped within the polymer matrix.

A portion of a 15 mm connector can be coated with an inactive material that is insensitive to $CO_2$ and water from expired breath and colorimetrically identical to the unreacted matrix. The inactive material serves as a reminder of the pre-activated color when the active matrix responds to expired $CO_2$ and water and changes color. Some examples of providing a color reminder or comparator are as follows: coating the front portion of the connector with active matrix and the back portion with inactive matrix and forming the two matrices in various patterns such as swirls, logo designs, etc. The inactive matrix may be applied by simply over-coating the active matrix with a gas impermeable or water vapor impermeable substance. Alternatively, a second dye could be used which is similar in color but unresponsive. Another way of dramatizing the color change which may be used with cuffed tracheal tubes is to make the pilot balloon the same color as the indicator matrix.

With reference now to the drawings, in FIG. 1, an endotracheal tube circuit comprises a transparent endotracheal tube 10, a 15 mm connector 12, a sensor fitting 14 and a ventilation tubing 22. Two possible locations for the $CO_2$ indicator matrix are shown, one being a coating 20a on the inside surface of the transparent endotracheal tube 10. However, if desired, indicator material 20 can be injected into a groove 24 formed in the sensor fitting 14. In the latter case, the indicator is preferably injected in a liquid state and allowed to gel, fixing it in location. The fitting can either be left in place or disposed of after confirming endotracheal tube placement.

Figure 2:
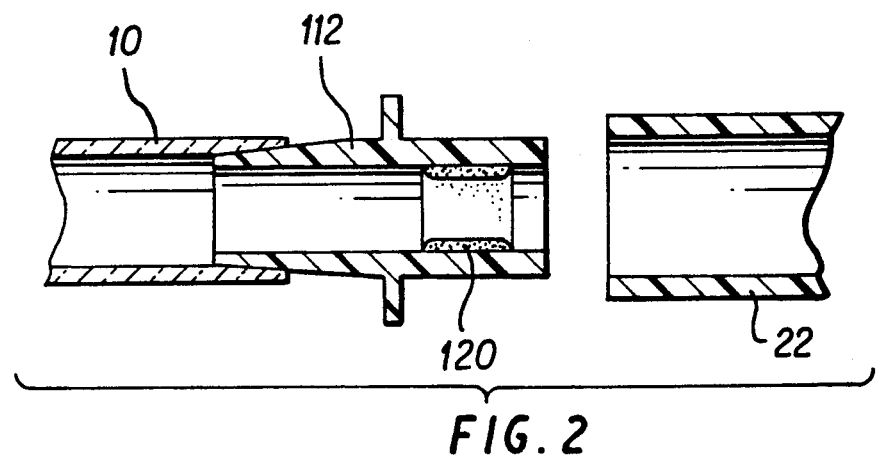
FIG. 2 shows a partially exploded, cross-sectional view of a second embodiment of the invention.

Either or both of the locations shown in FIG. 1 can be utilized for positioning of the $CO_2$ indicator matrix, or one or more other suitable locations in the respiratory circuit can be used. For example, FIG. 2 shows another embodiment of the invention in which the indicator matrix 120 is part of a 15 mm connector 112 connected to endotracheal. In this embodiment the indicator matrix 120 is applied as a thin film using a "spin"

technique and allowed to dry out completely. The 15 mm connector 112 is connectable to ventilation tubing 22 and is preferably molded out of a clear material, such as an acrylic plastic or polycarbonate to allow the color change of the indicator to be visible. Particularly preferred plastics are polyacrylonitrile/methacrylate (Barex 210, manufactured by Sohio), acrylic multipolymers such as G-20 (Cyro Industries), XT-800 (Cyro Industries), NAS (Richardson Polymer Corporation), and RSA-3G (Richardson Polymer Corporation). These polymers are particularly preferred because they contain methacrylate based polymers which increase the adherence of the matrix to the connector.

Figure 3:
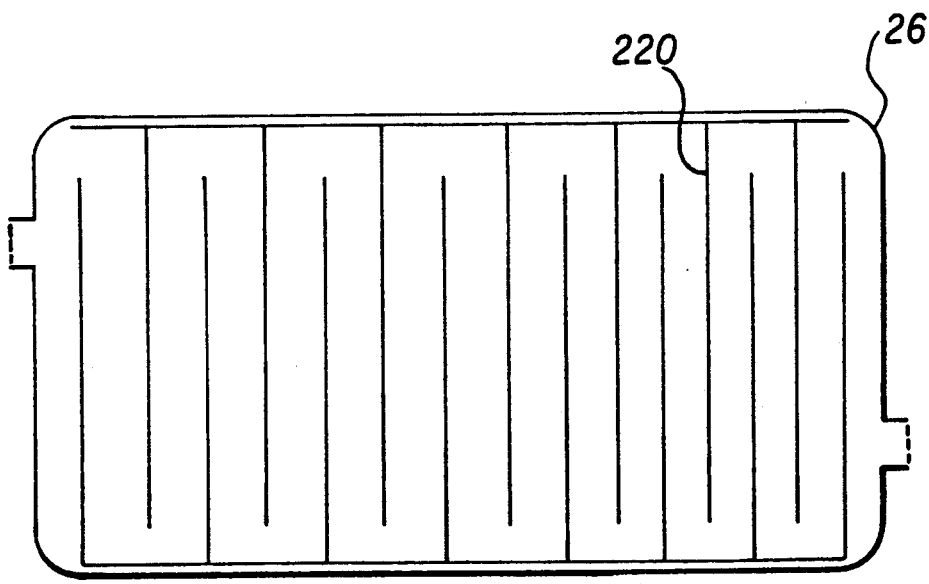
FIG. 3 schematically illustrates a heat/moisture exchanger for a respiratory circuit, containing a pH indicating material in accordance with a third embodiment of the invention.

FIG. 3 shows another embodiment wherein a heat-/moisture exchanger for a respiratory circuit includes a transparent housing 26 that contains a matrix material 220 having an indicator dye present therein that changes color when exposed to exhaled $CO_2$.

Figure 5:
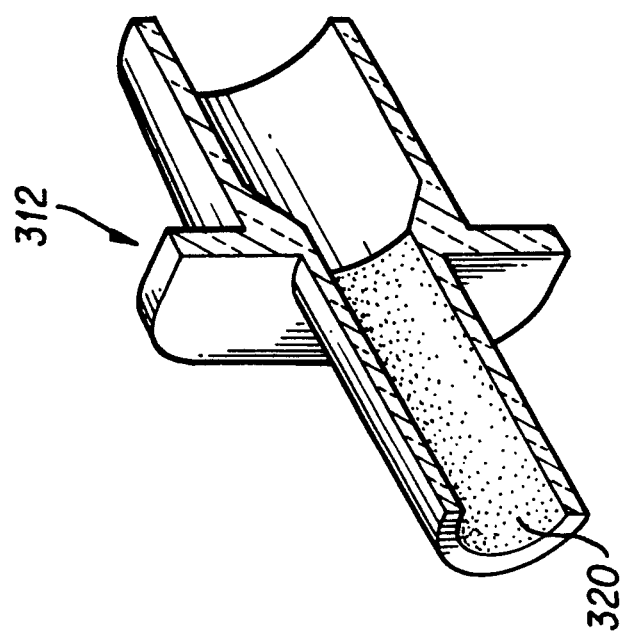
FIG. 5 shows a cross-sectional view of the embodiment of FIG. 4.
Figure 4:
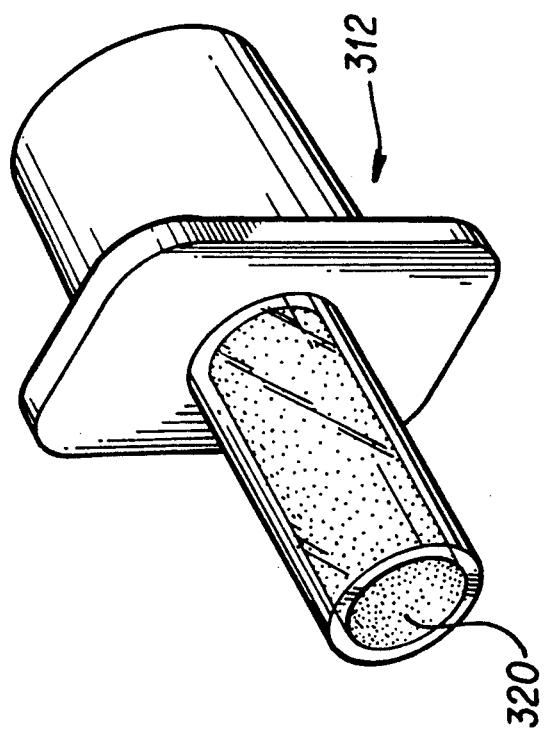
FIG. 4 shows a perspective view of a fourth embodiment of the invention.

FIGS. 4 and 5 show yet another embodiment in which the indicator 320 is part of a 15 mm connector 312. In this embodiment, the matrix 320 may be UV-curable, and is applied to the inside diameter of the front portion of the connector 312.

Figure 7:
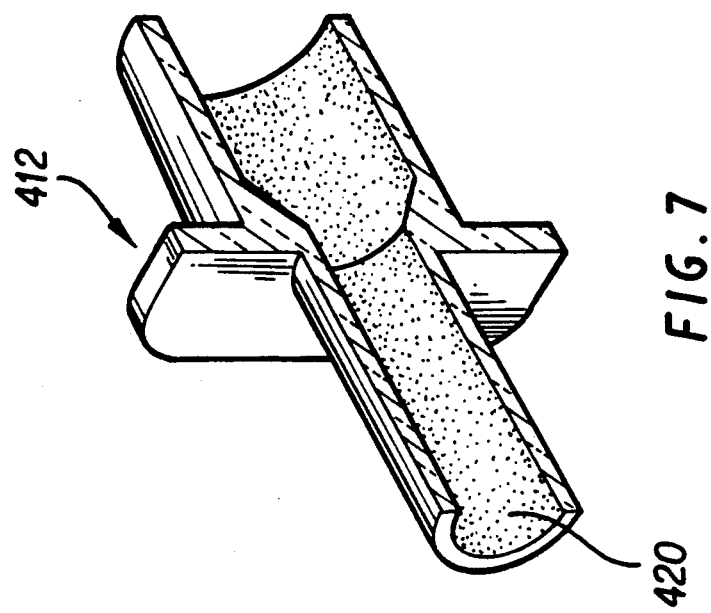
FIG. 7 shows a cross-sectional view of the embodiment shown in FIG. 6.
Figure 6:
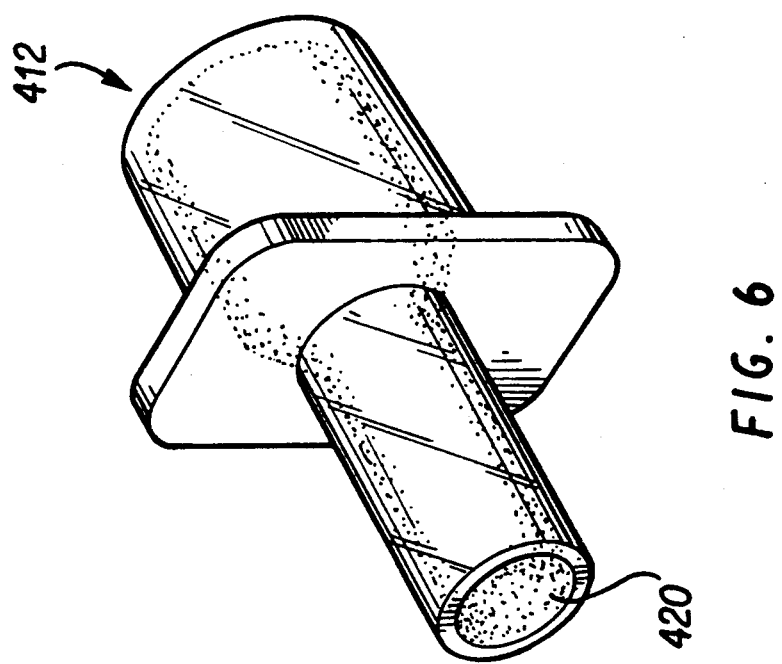
FIG. 6 shows a perspective view of a fifth embodiment of the invention.

FIGS. 6 and 7 show still another embodiment wherein a UV-curable matrix 420 is applied to the entire inside diameter of a connector 412.

As will be apparent from the above discussion, the present invention provides a substantial advantage over the prior art, in that the indicator can be applied to an endotracheal tube, connector, sensor fitting or at any suitable location in a respiratory circuit, in a simple fashion. Also, because it can be activated by moisture present in the patient's expired breath, the invention can be stored and shipped in a dry condition, ready for use.

The carbon dioxide indicators of the present invention have exceptional performance characteristics, including deep starting colors and quick recovery times to their original color upon cessation of exposure to carbon dioxide and water. Without being bound to any particular theory, these phenomena may result from there being relatively low amounts of residual water in the polymer due to increased hydrophobicity. In preferred embodiments, incorporating hydrophobic polymers which are methacrylate based and contain alkyl side groups of up to twelve carbon atoms in length, imparts exceptional performance characteristics to the carbon dioxide indicator matrix. Additionally, the wash-off rate of the indicator from the inner surface of the device during use may be improved as well.

The invention is further illustrated by the following examples, which are not intended to be limiting.

EXAMPLE I

An indicator material having the following components (by wt. %) was made:
- 6% polyvinylpyrrolidone (360,000 M.W.)
- 0.4% o-cresolphtalein complexon sodium salt
- 93.6% distilled water Drops of the indicator were placed onto a polyurethane tube and allowed to dry (in an oven at 60° C. for 2 hr.). The indicator changed from purple-red to clear after 4-5 respirations. The indicator changed color when dry, using only the moisture of respired breath.

EXAMPLE II

An embodiment using a cationic or basic methacrylate hydrogel.

An indicator having the following components (by wt. %) was made:
- 15.5% methyl chloride quaternary salt of dimethylaminoethyl methacrylate (MQ6)
- 1.5% o-cresolphthalein complexon sodium salt (141-OCC)
- 83.0% distilled water This was applied (by spin coating) at a surface concentration of 0.05 cc/cm$^2$ to the inside diameter of the front half of a polycarbonate 15 mm connector. The indicator responded in 3-4 breaths (purple-red to clear) and recovered in 15-30 minutes. The indicator cured (i.e. the water evaporated) in 20 minutes (a heating element at 80° C. was brought to within 4 mm of the inside surface where the coating had been applied).

EXAMPLE III

An example using the preferred cationic or basic polymer in a more volatile solvent system (a faster evaporating solvent improves processing time.)

An indicator having the following components (by wt. %) was made:
- 2% MQ6
- 3% 141-OCC
- 15% distilled water
- 80% methanol The indicator was applied to 15 mm connectors fashioned from various transparent materials in surface concentrations of 0.05-0.10 cc/cm$^2$. The matrix responded in 1-3 breaths (pale blue to clear) and reversed in less than 5 seconds. The matrix cured in <4 minutes (heat applied as in Example II). Although the response of the indicator was good, due to the minimal presence of hydrogel, the matrix was highly water soluble and therefore would begin to wash away after 50 breathing cycles.

EXAMPLE IV

An example using a basic salt to achieve more vivid color.

An indicator having the following components (by wt. %) was made:
- 7.5% MQ6
- 1.0% 141-OCC
- 53.8% methanol
- 37.4% distilled water
- 0.3% sodium hydroxide The indicator was applied in surface concentrations of 0.06 cc/cm$_2$. The color changed from purple-blue to clear in 1 breath and recovered in 20 seconds. The matrix cured in <3 minutes. As a result of the greater polymer concentration the matrix was not as susceptible to water solubility.

EXAMPLE V

This example used a polymer which contained a small percentage of a hydrophobic monomer in order to better resist water solvation as well as to better withstand ethylene oxide sterilization.

Components by weight percent:
- 5.0% MQ6
- 0.1% lauryl methacrylate
- 1.3% 141-OCC
- 0.1% sodium hydroxide
- 92.2% methanol
- 1.3% distilled water The matrix was applied to 15 mm connectors in surface concentrations of 0.05 cc/cm$^2$. The indicator responded to a water saturated gas stream containing 2% CO₂ (at a flow rate <2 liters/minute and at a temperature of 35° C.) in 5 seconds (changed from purple-blue to clear). The indicator recovered in <15 seconds. The matrix cured in <1.5 minutes.

All the above examples have been shown to not respond to dry carbon dioxide gas, even at concentrations of 10%. Also, all of the indicators have been shown to not respond to water saturated (at 35° C.) 100% nitrogen gas.

EXAMPLE VI

A matrix having the following components (by weight %) was made:
- 19% methyl chloride quaternary salt of dimethylaminoethyl methacrylate (MQ6)
- 10% methyl methacrylate (MMA)
- 1% lauryl methacrylate (LMA)
- 1.2% O-cresolphthalein complexon sodium salt
- 0.2% sodium hydroxide
- 63.8% methanol
- 4.8% water This was applied (by spin coating) to the inside diameter of the front half of a 15 mm connector at a surface concentration of 0.004 g/cm². The matrix cured up in 15–20 seconds. The indicator responds in 1 breath (purple-blue to clear) and recovers in about 10 seconds upon cessation of exposure to expired breath.

Since many modifications, variations and changes in detail may be made to the described embodiments, it is intended that all matter in the foregoing description and shown in the accompanying drawings be interpreted as illustrative and not in a limiting sense.

What is claimed is:

1. A carbon dioxide indicator comprising a predominantly hydrophilic polymer matrix selected from the group consisting of alkyl methacrylate, alkyl halide quaternary salt of an alkyl methacrylate, copolymer of an alkyl halide quaternary salt of an alkyl methacrylate, polyurethane, polyvinylpyrrolidone, copolymer of polyvinylpyrrolidone, polyethylene oxide derivatives, copolymers of polyethylene oxide derivatives, polypropylene oxide derivatives, copolymers of polypropylene oxide derivatives, corn starch derivatives, copolymers of corn starch derivatives and any of the above polymers which have been crosslinked, and a pH-sensitive dye which indicates the presence of carbon dioxide comprising o-cresolpthalein or salt thereof present in said matrix, wherein said indicator is in a sufficient amount that it does not change color for at least 15 minutes when said indicator is exposed to normal ambient air, but does change color when said indicator is exposed to exhaled air, a color change in response to exposure to exhaled air being at least about 50 times more rapid than would occur with exposure of the indicator to normal ambient air alone.

2. The indicator of claim 1 wherein said polymer matrix is a polyurethane foam.

3. The indicator of claim 1 wherein said pH-sensitive dye is an o-cresolphthalein complexon sodium salt.

4. The indicator of claim 1 wherein said polymer matrix further comprises a solid desiccant.

5. The indicator of claim 1 wherein said indicator changes color upon exposure to two or less exhaled breaths of a patient.

6. The indicator of claim 1 wherein said indicator further comprises a heat-moisture exchanger in said matrix.

7. The indicator of claim 1 wherein said matrix further comprises less than about 30% by weight of a hydrophobic monomer.

8. The indicator of claim 1 wherein said matrix further comprises less than about 20% by weight of a hydrophobic monomer.

9. The indicator of claim 1 wherein said matrix further comprises less than about 10% by weight of a hydrophobic monomer.

10. The indicator of claim 1 wherein said matrix further comprises less than about 5% by weight of a hydrophobic monomer.

11. The indicator of claim 1 further including at least one basic salt present in said matrix.

12. The indicator of claim 11 where said basic salt is sodium hydroxide, potassium phosphate, trisodium phosphate or potassium hydroxide.

13. The indicator of claim 1 wherein said color change occurs in less than about five seconds of exposure to exhaled air.

14. The indicator of claim 13 wherein exhaled air has a carbon dioxide concentration of at least about 15 mm of Hg.

15. The indicator of claim 1 wherein said polymer matrix is UV cured and said matrix further comprises: a UV-curable methyl chloride quaternary salt of at least one methacrylate; a cross-linking agent; and a photoindicator.

16. The indicator of claim 15 wherein said at least one methacrylate is a dimethylaminoethyl methacrylate.

17. The indicator of claim 16 wherein said methyl chloride quaternary salt of dimethylaminoethyl methacrylate is at least 70% of said matrix and lauryl methacrylate comprises no more than 30% of the matrix.

18. The indicator of claim 1 wherein said hydrophilic polymer matrix comprises a hydrogel.

19. The indicator of claim 18 wherein said hydrogel comprises the methyl chloride quaternary salt of dimethylaminoethyl methacrylate.

20. The indicator of claim 18 wherein said polymer matrix further comprises a polyurethane foam.

21. The indicator of claim 1 wherein said matrix is an alkyl methacrylate in which the alkyl portion contains from 1 to about 12 carbon atoms.

22. The indicator of claim 21 wherein said alkyl methacrylate further comprises a hydrophobic portion of said matrix.

23. The indicator of claim 22 wherein the ratio of hydrophilic to hydrophobic portions of said matrix is about 2:1 by weight.

24. The indicator of claim 22 wherein said hydrophilic portion is comprised of an alkyl halide quaternary salt of an alkyl methacrylate.

25. The indicator of claim 22 wherein said pH-sensitive dye comprises o-cresolphthalein complexon sodium salt.

26. The indicator of claim 25 further including at least one basic salt present in said matrix.

27. The indicator of claim 26 wherein said at least one basic salt is sodium hydroxide, potassium phosphate, trisodium phosphate or potassium hydroxide.

28. The indicator of claim 27 wherein said basic salt is sodium hydroxide.

29. The indicator of claim 22 wherein said hydrophilic portion is comprised of a methyl chloride quaternary salt of dimethylaminoethyl methacrylate.

30. The indicator of claim 29 wherein the ratio of hydrophilic to hydrophobic portions of said matrix is about 2:1 by weight.

31. The indicator of claim 30 wherein the alkyl portion of the hydrophobic alkyl methacrylate contains from 1 to about 8 carbon atoms.

32. The indicator of claim 30 wherein the alkyl portion of the hydrophobic alkyl methacrylate contains from 1 to about 4 carbon atoms.

33. The indicator of claim 30 wherein the hydrophobic alkyl methacrylate comprises ethyl methacrylate.

34. The indicator of claim 33 wherein the hydrophobic alkyl methacrylate further comprises lauryl methacrylate.

35. The indicator of claim 30 wherein the hydrophobic alkyl methacrylate is a methyl methacrylate.

36. The indicator of claim 35 wherein the hydrophobic alkyl methacrylate further comprises lauryl methacrylate.

37. A carbon dioxide indicator device comprising an indicator housing, and an indicator within the housing, said indicator comprising a predominantly hydrophilic polymer matrix selected from the group consisting of alkyl methacrylate, alkyl halide quaternary salt of an alkyl methacrylate, copolymer of an alkyl halide quaternary salt of an alkyl methacrylate, polyurethane, polyvinylpyrrolidone, copolymer of polyvinylpyrrolidone, polyethylene oxide derivatives, copolymers of polyethylene oxide derivatives, polypropylene oxide derivatives, copolymers of polypropylene oxide derivatives, corn starch derivatives, copolymers of corn starch derivatives and any of the above polymers which have been crosslinked, and a pH-sensitive dye which indicates the presence of carbon dioxide comprising o-cresolpthalein or salt thereof present in said matrix, wherein said indicator is in a sufficient amount that it does not change color for at least 15 minutes when said indicator is exposed to normal ambient air, but does change color when said indicator is exposed to exhaled air, a color change in response to exposure to exhaled air being at least about 50 times more rapid than would occur with exposure of the indicator to normal ambient air alone.

38. The device of claim 37 wherein said polymer matrix is a polyurethane foam.

39. The device of claim 37 wherein said pH-sensitive dye is an o-cresolphthalein complexon sodium salt.

40. The device of claim 37 wherein said indicator housing is part of an endotracheal tube circuit.

41. The device of claim 37 wherein said indicator housing is an endotracheal tube.

42. The device of claim 37 wherein said polymer matrix further comprises a solid desiccant.

43. The device of claim 37 wherein said indicator housing further is a connector having at least one end capable of being connected to an endotracheal tube.

44. The device of claim 37 wherein said indicator changes color upon exposure to two or less exhaled breaths of a patient.

45. The device of claim 37 wherein said housing has an interior surface and said indicator is applied to the interior surface of said housing.

46. The device of claim 37 wherein said matrix further comprises less than about 30% by weight of a hydrophobic monomer.

47. The device of claim 37 wherein said matrix further comprises less than about 20% by weight of a hydrophobic monomer.

48. The device of claim 37 wherein said matrix further comprises less than about 10% by weight of a hydrophobic monomer.

49. The device of claim 37 wherein said matrix further comprises less than about 5% by weight of a hydrophobic monomer.

50. The device of claim 37 wherein said indicator further includes at least one basic salt present in said housing.

51. The device of claim 50 wherein said basic salt is sodium hydroxide, potassium phosphate, trisodium phosphate or potassium hydroxide.

52. The device of claim 37 wherein said color change occurs in less than about five seconds of exposure to exhaled air.

53. The device of claim 52 wherein said exhaled air has a carbon dioxide concentration of at least about 15 mm of Hg.

54. The device of claim 37 wherein said polymer matrix is UV-cured and said matrix further comprises: a UV-curable methyl chloride quaternary salt of at least one methacrylate; a cross-linking agent; and a photoinitiator.

55. The device of claim 54 wherein said at least one methacrylate is a dimethylaminoethyl methacrylate.

56. The device of claim 55 wherein the methyl chloride quaternary salt of dimethylaminoethyl methacrylate is at least 70% of said matrix and lauryl methacrylate comprises no more than 30% of the matrix.

57. The device of claim 37 wherein said hydrophilic polymer matrix comprises a hydrogel.

58. The device of claim 37 wherein said hydrogel comprises methyl chloride quaternary salt of dimethyl methacrylate.

59. The device of claim 58 wherein said polymer matrix further comprises a polyurethane foam.

* * * * *

UNITED STATES PATENT AND TRADEMARK OFFICE
CERTIFICATE OF CORRECTION

PATENT NO. : 5,124,129  Page 1 of 2

DATED : June 23, 1992

INVENTOR(S) : Riccitelli et al.

It is certified that error appears in the above-identified patent and that said Letters Patent is hereby corrected as shown below:

On the cover page, under "Related U.S. Application Data", line 4, delete "325,754", and insert --225,754--.

Column 2, line 59, delete "exhale" and insert --exhaled--.

Column 3, line 66, after "sodium", insert --salt--.

Column 5, line 1, delete "utilizes" and insert --utilized--.

Column 6, line 67, after "endotracheal", insert --tube 10--.

UNITED STATES PATENT AND TRADEMARK OFFICE
CERTIFICATE OF CORRECTION

PATENT NO.  : 5,124,129
DATED       : June 23, 1992
INVENTOR(S) : Riccitelli et al.

It is certified that error appears in the above-identified patent and that said Letters Patent is hereby corrected as shown below:

Column 12:

Claim 58, line 1, delete "37", and insert --57--.

Claim 59, line 1, delete "58", and insert --57--.

Signed and Sealed this

Twenty-fifth Day of January, 1994

Attest:

BRUCE LEHMAN

*Attesting Officer*      *Commissioner of Patents and Trademarks*